United States Patent
Schwammberger et al.

(10) Patent No.: US 9,775,655 B2
(45) Date of Patent: Oct. 3, 2017

(54) INTRAMEDULLARY NAIL ASSEMBLY

(71) Applicant: ZIMMER GMBH, Winterthur (CH)

(72) Inventors: Andy Schwammberger, Niederdorf (CH); Reto Senger, Winterthur (CH)

(73) Assignee: ZIMMER GMBH (CH)

( * ) Notice: Subject to any disclaimer, the term of this patent is extended or adjusted under 35 U.S.C. 154(b) by 76 days.

(21) Appl. No.: 14/633,436

(22) Filed: Feb. 27, 2015

(65) Prior Publication Data

US 2015/0272636 A1 Oct. 1, 2015

(30) Foreign Application Priority Data

Mar. 31, 2014 (EP) ..................................... 14162715

(51) Int. Cl.
*A61B 17/56* (2006.01)
*A61B 17/58* (2006.01)
*A61F 2/30* (2006.01)
*A61B 17/72* (2006.01)

(52) U.S. Cl.
CPC ...... *A61B 17/7241* (2013.01); *A61B 17/7283* (2013.01)

(58) Field of Classification Search
CPC .. A61B 17/72; A61B 17/7233; A61B 17/7241
USPC ................................................ 606/62–64, 95
See application file for complete search history.

(56) References Cited

U.S. PATENT DOCUMENTS

2002/0151898 A1* 10/2002 Sohngen ................ A61B 17/68
606/62
2012/0109127 A1* 5/2012 Overes ............... A61B 17/7241
606/64

FOREIGN PATENT DOCUMENTS

DE 2246274 3/1974
WO WO-0143652 A1 6/2001

* cited by examiner

*Primary Examiner* — Ellen C Hammond
*Assistant Examiner* — Christina Negrellirodrigue
(74) *Attorney, Agent, or Firm* — Schwegman Lundberg & Woessner, P.A.

(57) ABSTRACT

The present disclosure provides an intramedullary nail assembly comprising an intramedullary nail and an insert sleeve. The intramedullary nail has a nail longitudinal axis and comprises a cavity being accessible from a nail proximal end, the cavity being confined by a nail inner wall, the cavity having a cavity longitudinal axis. The nail inner wall is provided with a predominantly longitudinal groove and a predominantly transverse groove, the transverse groove and the longitudinal groove communicating with each other at a junction. The insert sleeve is configured to be received within the cavity and comprises a cam radially protruding from the insert sleeve and sized to mate with each of the longitudinal and transverse grooves such that the cam is displaceable within the longitudinal groove from a longitudinal groove proximal end to the junction and is further displaceable towards a terminal end of the transverse groove.

16 Claims, 3 Drawing Sheets

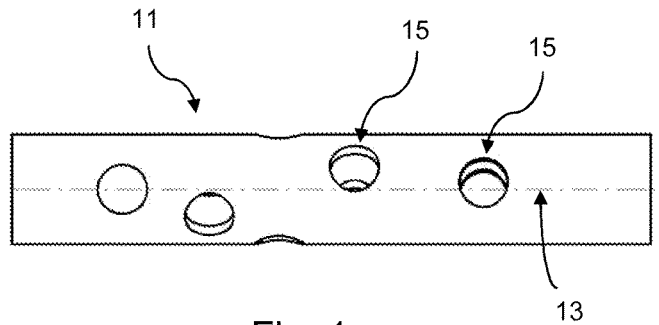
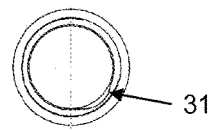
Fig. 1  Fig. 2
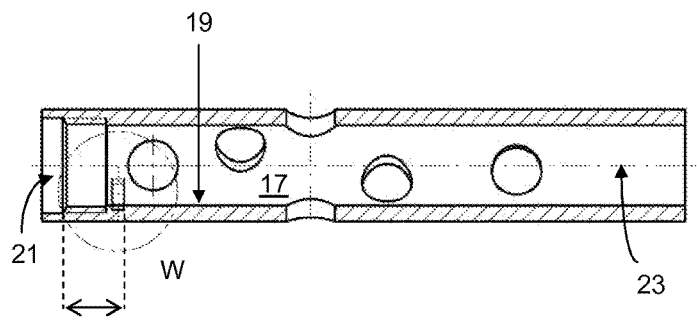
Fig. 3
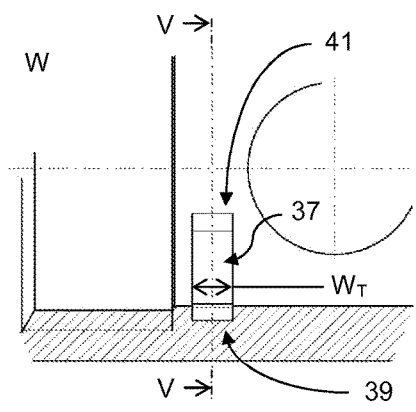
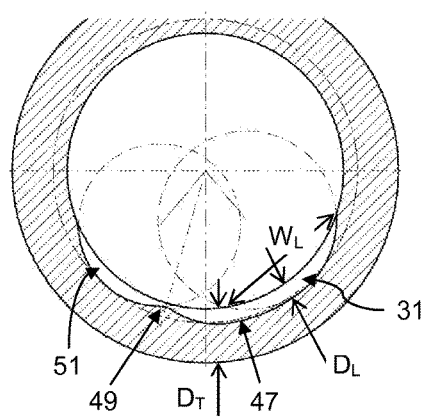
Fig. 4  Fig. 5

INTRAMEDULLARY NAIL ASSEMBLY

RELATED APPLICATIONS

This application claims the benefit of priority under 35 U.S.C. 119 to European Patent Application No. 14162715.8, filed on Mar. 31, 2014, the benefit of priority of which is claimed hereby, and which is incorporated by reference herein in its entirety.

BACKGROUND

1. Field of the Disclosure

The present disclosure relates to orthopedic implants, and more particularly, to intramedullary nail assemblies.

2. Description of the Related Art

Intramedullary nails may be used to align and stabilize fractures of a long bone, such as a humerus. In a fractured humerus, an intramedullary nail may be inserted into the intramedullary canal of the humerus and positioned to extend across the fracture line of the humerus. Then, locking screws or other securement devices may be inserted through transverse throughholes formed in the intramedullary nail on opposing sides of the fractured humerus to secure the opposing portions of the fractured humerus together.

To secure the locking screws to in the intramedullary nail, the intramedullary nail may have a cavity accessible from the proximal end of the nail, wherein an insert sleeve is sized and shaped for insertion into the cavity. The insert includes transverse locking holes which are aligned with the transverse throughholes of the nail when the insert sleeve is in the desired position within the cavity of the nail. The transverse locking holes of the insert sleeve have a smaller diameter than the locking screws used to lock the intramedullary nail in a bone. Therefore, the thread of the locking screw cuts into the wall of the insert sleeve, or is firmly received therein, which limits the respective transverse locking hole so that the locking screws are secured against loosening within the transverse locking holes and consequently within the locking holes of the intramedullary nail. Thus, firm fixation of the locking screws in the intramedullary nail can be achieved. As will be contemplated by the skilled person also a tight fit of an unthreaded shank of a locking screw or other transverse locking element will fit said purpose.

Such an intramedullary nail assembly is disclosed in US 2012/0109127 A1. In this document, to secure the insert sleeve within the cavity of the intramedullary nail, the cavity includes an axial stop to prevent the insert sleeve from moving distally therepast and a head space includes an internal thread at the proximal end of the nail for engaging a set screw which prevents the insert sleeve from loosening from the cavity. In addition, in said document, the insert sleeve includes an eccentric nose at the distal end which engages a complementary shaped eccentric portion in the cavity which allows the transverse locking holes in the insert sleeve to be exactly aligned with the transverse throughholes in the proximal end of the intramedullary nail.

SUMMARY

The present disclosure provides an intramedullary nail assembly comprising an intramedullary nail and an insert sleeve. The intramedullary nail has a nail longitudinal axis and comprises a cavity being accessible from an nail proximal end. The cavity is confined by a nail inner wall and has a cavity longitudinal axis. The nail inner wall is provided with a predominantly longitudinal groove and a predominantly transverse groove. The predominantly transverse groove and the predominantly longitudinal groove communicate with each other at a junction. The junction is common to the predominantly longitudinal groove and the predominantly transverse groove. Each of the grooves has a length, a width, and a depth. The predominantly longitudinal groove is accessible from a cavity proximal end. This in particular means that the predominantly longitudinal groove comprises an opening at a proximal face allowing to introduce a male element into the predominantly proximal groove in a proximally-distally oriented movement. The insert sleeve is configured to be received within the cavity and comprises a cam. The cam radially protrudes from the insert sleeve, in particular with respect to an insert sleeve longitudinal axis, and is sized to mate with each of the predominantly longitudinal and predominantly transverse grooves such that the cam is displaceable within the predominantly longitudinal groove from a predominantly longitudinal groove proximal end to the junction and is further displaceable towards a terminal end of the predominantly transverse groove.

The interaction of the cam and the grooves of the intramedullary nail assembly according to the present disclosure enables to secure the insert sleeve within the cavity of the intramedullary nail and at the same time to exactly align transverse locking holes of the insert sleeve with transverse throughholes in the intramedullary nail. A set screw or other retaining element for preventing the insert sleeve from loosening from the cavity is not required, but may additionally be provided, e.g. from radial through the nail wall or axially from the proximal end of the nail. The intramedullary nail assembly according to the present disclosure provides a coupling or fastening mechanism between the intramedullary nail and the insert sleeve which is easy to handle and easy to manufacture. In particular, the interacting cam and grooves may resemble or define a bayonet-type lock.

In particular, the predominantly longitudinal groove is defined by a groove which forms an angle with the cavity longitudinal axis of 45° or less, in particular 30° or less, in particular 15° or less, in particular 5° or less, in particular 2° or less, in particular at least approximately 0°. In particular, the predominantly transverse groove is defined by a groove which forms an angle with the cavity longitudinal axis of 45° or more, in particular 60° or more, in particular 75° or more, in particular 85° or more, in particular 88° or more, in particular at least approximately 90°. In particular, the term "mate with each of" defines that the cam can be inserted into any of the predominantly longitudinal and transverse grooves, that is, can be moved between the predominantly longitudinal groove and the predominantly transverse groove.

Each of the predominantly longitudinal and transverse grooves may be straight, bend or comprise both straight and bend sections. The transition between the predominantly longitudinal groove and the predominantly transverse groove may be a continuous curve or may be angled or wedge shaped. In particular, the predominantly longitudinal groove has a proximal end and a distal end and/or the predominantly transverse groove has a communicating end and a terminal end. The proximal end of the predominantly longitudinal groove may open out in an axial direction and thus provide access for introducing a male element.

The cavity may be accessible from the nail proximal end via a head space provided at the proximal end of the intramedullary nail. In particular, an inside dimension of the head space, in particular a diameter of the head space, may be larger than that of the cavity. It will be understood that the cavity may also end flush with the nail proximal end and thus no head space will be present.

In particular, the longitudinal groove is axially open at its proximal end. In particular, the proximal end of the predominantly longitudinal groove coincides with and/or defines the proximal end of the cavity. The proximal end of the cavity may be positioned distally from the proximal end of the intramedullary nail. In the inserted state, the proximal end of the insert sleeve may be positioned distally from the proximal end of the cavity.

The insert sleeve may be made of polyether ether ketone (PEEK), Polyethylene (PE) or any other suitable material, in particular any other suitable polymer material. A set screw or any other type of closure device such as a lid or a cap may be provided to close the proximal end of the cavity. The closure device may be positioned in the above-mentioned head space and/or with or without clearance to the insert sleeve.

Throughout the present application the positional terms "distal" and "proximal" will be used to describe a direction away from (distal) and toward (proximal) a surgeon of the intramedullary nail assembly, respectively, and/or a leading (distal) end and a trailing end (proximal) of the intramedullary nail assembly when inserted into a human body, respectively.

In an aspect, the predominantly longitudinal groove extends in parallel to the cavity longitudinal axis and/or the predominantly transverse groove extends orthogonally to the cavity longitudinal axis. In another aspect, the predominantly longitudinal groove and the predominantly transverse groove form a right angle with each other, and in particular form a right-angled wedge. When forming a right-angled wedge, both, the predominantly longitudinal groove and the predominantly transverse groove, have one end in common defining the junction. The predominantly longitudinal and transverse grooves may be arranged to form an L-shape. In another aspect, the predominantly transverse groove connects to and/or adjoins a distal end of the predominantly longitudinal groove. In particular, a communicating end of the predominantly transverse groove connects to and/or adjoins the distal end of the predominantly longitudinal groove.

In another aspect, the nail longitudinal axis and the cavity longitudinal axis are parallel with each other, and in particular coincide.

In another aspect, at least a section of the transverse groove forms a seat for snugly receiving the cam in a locked position, and/or the predominantly transverse groove comprises a groove base, the groove base, along a part of the length of the predominantly transverse groove, extending radially inwardly thus reducing the depth of the predominantly transverse groove such as to form a hump within the predominantly transverse groove.

The hump may be arranged between the junction, in particular a communicating end of the predominantly transverse groove, and the terminal end of the predominantly transverse groove, the hump being configured and sized to reversibly and radially inwardly displace and/or deform the cam of the insert sleeve while the cam travels from the junction towards the terminal end of the predominantly transverse groove. In particular, the hump is arranged between the seat and the junction, in particular a communicating end of the predominantly transverse groove, and in particular delimits the seat from the junction. The seat may be formed between the hump and the terminal end of the predominantly transverse groove.

In another aspect, the seat has a length and a depth and the predominantly longitudinal groove has a width and a depth, wherein at least one of the following conditions is fulfilled: a) the width of the predominantly longitudinal groove at the junction with the predominantly transverse groove is greater than the length of the seat; b) the depth of the predominantly longitudinal groove at the junction with the predominantly transverse groove is greater than the depth of the seat. That is, while the seat snugly receives the cam the cam has sufficient play to be readily displaced within the predominantly longitudinal groove and in a further aspect also within the predominantly longitudinal groove. It will be appreciated that also a sufficient play of the cam within the predominantly transverse groove, apart from the hump and the seat, will facilitate the displacement of the cam within the groove and thus the displacement of the cam towards the seat.

In another aspect, at least one of the predominantly longitudinal groove and the predominantly transverse groove, in particular a width and/or a depth thereof, tapers from the proximal end towards a distal end or from a communicating end towards the terminal end, respectively. Thus, a funnel for the cam is provided and the cam has sufficient play within the grooves, apart from the hump and the seat, and the displacement of the cam within the predominantly longitudinal groove and/or within the predominantly transverse groove is facilitated.

In another aspect, the nail inner wall is provided with a plurality of sets of predominantly longitudinal and predominantly transverse grooves, the insert sleeve having a same plurality of cams radially protruding from it, a circumferential distribution of the cams being the same as that of the sets of grooves, each cam being sized to matingly engaging a respective set of grooves. In particular, the plurality of sets of grooves and the plurality of cams are unevenly distributed in circumferential direction such that each cam is unambiguously assigned to a set of grooves and the insert sleeve may only be received within the cavity in a well-defined circumferential orientation. The circumferential extension of a predominantly transverse groove from a communicating end to the seat may be identical for each set of grooves.

In another aspect, in particular in case only one cam and only one predominantly transverse groove are provided, the circumferential extension of a predominantly transverse groove from a communication end to a seat is less than 120°, in particular between 120° and 40°, in particular between 100° and 60°. In particular in case more than one cam and more than one predominantly transverse groove are provided, the circumferential extension of a predominantly transverse groove from a communication end to a seat is less than 90°, in particular between 75° and 15°, in particular between 65° and 25°.

In another aspect, the insert sleeve is provided at a proximal end thereof with a engagement reception for engagement of a tool for inserting the insert sleeve into the cavity and/or with a rotation reception for engaging a tool for rotating the insert sleeve and effecting the final locking displacement of the cam within the predominantly transverse groove. The rotation reception may reach further into the insert sleeve than the engagement reception.

In another aspect, the cam or at least one cam is provided at a proximal end of the insert sleeve. In case of a plurality of cams, all cams may be provided at the same axial position with respect to an insert sleeve longitudinal axis or at least partly at different axial positions. Accordingly, the predominantly transverse grooves may be provided at the same axial position with respect to the cavity longitudinal axis or at least partly at different axial positions.

In another aspect, the insert sleeve and the cavity have cross sectional dimensions adapted to each other such that the insert sleeve is received within the cavity essentially without play, and in particular have corresponding cross sections.

In another aspect, at least one of the insert sleeve and the cavity has a cross section in the shape of one of a circle and a truncated circle.

In another aspect, the intramedullary nail and the insert sleeve comprise at least one transverse throughhole in the nail and at least one transverse locking hole in the sleeve, respectively, wherein the positions and axes of a respective transverse locking hole and a respective transverse throughhole coincide in a locked position of the insert sleeve. In particular, the axes of the at least one transverse throughhole and the at least one transverse locking hole are oriented transverse to the nail longitudinal axis. Said through hole and locking hole axis may be perpendicular to the nail longitudinal axis or may be tilt with respect to the nail longitudinal axis in a proximal-distal direction. As will be well understood one or more sets of a through hole and a locking hole with perpendicular axes and one or more sets of a through hole and a locking hole with tilt axis may be arranged in one nail assembly.

In another aspect, the diameter of the at least one transverse locking hole is smaller than that of the at least one transverse throughhole.

The present disclosure further relates to an intramedullary nail for an intramedullary nail assembly as described above, having a nail longitudinal axis and comprising a cavity being accessible from a nail proximal end, the cavity being confined by an nail inner wall, the cavity having a cavity longitudinal axis, wherein the nail inner wall is provided with a predominantly longitudinal groove and a predominantly transverse groove, the predominantly transverse groove and the predominantly longitudinal groove communicating with each other at a junction common to the predominantly longitudinal groove and the predominantly transverse groove, each of the grooves having a length, a width, and a depth, the predominantly longitudinal groove being accessible from a cavity proximal end.

The present disclosure further relates to an insert sleeve for an intramedullary nail assembly as described above, comprising a cam, the cam radially protruding from the insert sleeve.

BRIEF DESCRIPTION OF THE DRAWINGS

The above-mentioned and other features and advantages of this disclosure, and the manner of attaining them, will become more apparent and the disclosure itself will be better understood by reference to the following description of embodiments of the disclosure taken in conjunction with the accompanying drawings, wherein:

FIG. 1 is a side view of an intramedullary nail of the present disclosure according to one exemplary embodiment;

FIG. 2 is a top view of the intramedullary nail of FIG. 1;

FIG. 3 is a cross-sectional side view of the intramedullary nail of FIG. 1;

FIG. 4 is a detail W of the cross-sectional side view of FIG. 3;

FIG. 5 is a cross-sectional view of the intramedullary nail of FIG. 4 taken along line V-V in FIG. 4;

Corresponding reference characters indicate corresponding parts throughout the several views. The exemplifications set out herein illustrate preferred embodiments of the disclosure and such exemplifications are not to be construed as limiting the scope of the disclosure in any manner.

DETAILED DESCRIPTION

Figure 6:
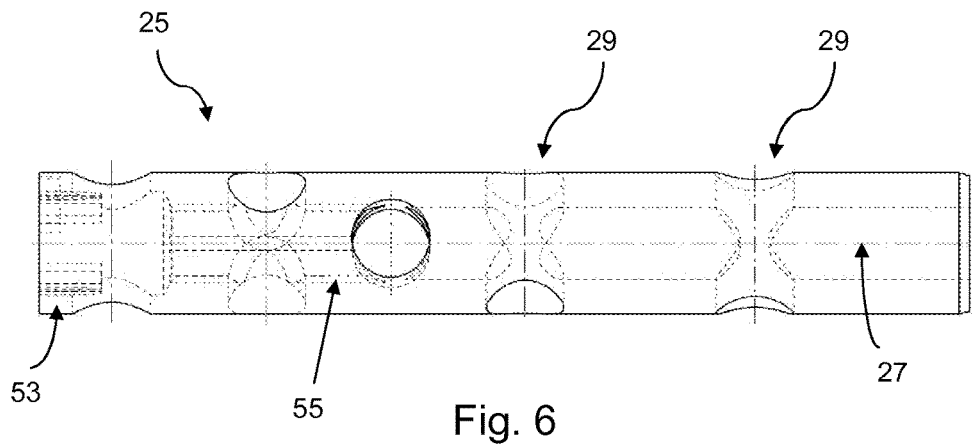
FIG. 6 is a side view of an insert sleeve insertable into the intramedullary nail of FIG. 1.

Referring to FIGS. 1 to 5, an intramedullary humeral nail 11 forming a substantially cylindrical, elongate body and extending along a nail longitudinal axis 13 is shown. Intramedullary nail 11 may be made of titanium alloy, such as Ti-6 Al-4 V, or any other biocompatible orthopedic material, such as medical grade stainless steel or a cobalt-chromium alloy. Transverse throughholes 15 extend through the intramedullary nail 11 transversely to the nail longitudinal axis 13 for receiving locking screws or any other suitable transverse locking element therein (not shown) which e.g. prevent rotation within and/or removal of intramedullary nail 11 from an intramedullary canal of a humerus and/or lock bone fragments. The transverse throughholes 15 are provided at different axial positions with respect to the nail longitudinal axis 13 and staggered relative to each other in circumferential direction.

The humeral nail 11 includes a circular cavity 17 which is defined by an inner wall 19 and accessible from the proximal end of the intramedullary nail 11 via a head space 21 provided at the proximal end of the intramedullary nail 11. The cavity 17 extends coaxially with the nail longitudinal axis 13, i.e. the cavity 17 has a cavity longitudinal axis 23 that coincides with the nail longitudinal axis 13. The proximal end of the cavity 17 is positioned distally from the proximal end of the intramedullary nail 11. The head space 21 has a diameter that is larger than the diameter of the cavity 17 such that a annular step is formed in between the head space 21 and the cavity 17. In a particular embodiment, the head space 21 may be omitted from the intramedullary nail 11.

Figure 7:
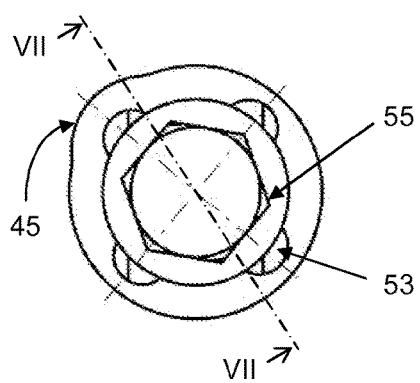
FIG. 7 is a top view of the insert sleeve of FIG. 6.
Figure 8:
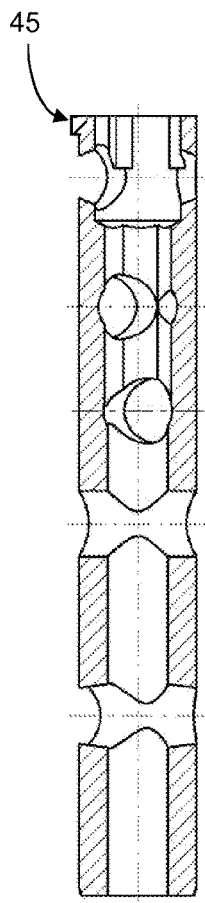
FIG. 8 is a cross-sectional view of the intramedullary nail of FIG. 7 taken along line VIII-VIII in FIG. 7.
Figure 9:
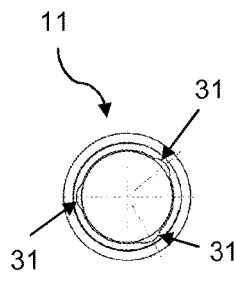
FIG. 9 is a top view of an intramedullary nail of the present disclosure according to another exemplary embodiment.

Referring to FIGS. 6 to 8, an insert sleeve 25 having an insert longitudinal axis 27 and a plurality of locking holes 29 is shown. The insert sleeve 25 has a circular cross-section with an outer diameter essentially equal to the diameter of the cavity 17 and is coaxially insertable into the cavity 17 of the intramedullary nail 11 to reach an inserted but unlocked intermediate position, the insert sleeve 25 being lockable in the cavity 17 and consequently in the intramedullary nail 11 by rotating the insert sleeve 25 about the insert longitudinal axis 27 from the intermediate position into a locked position as will be explained in more detail below.

In the locked position, the locking holes 29 of the insert sleeve 25 are automatically aligned with the transverse throughholes 15. Locking screws (not shown) having an outer thread diameter smaller than that of the transverse throughholes 15 and larger than that of the locking hole 29 may then be inserted through the transverse throughholes 15 thereby cutting into or being received in a tight fit by the walls limiting the locking holes 29. This allows the screws to be securely fixed within the intramedullary nail 11 without play.

Figure 10:
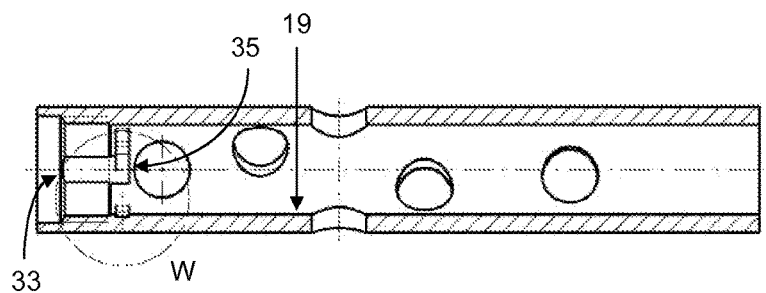
FIG. 10 is a cross-sectional side view of the intramedullary nail of FIG. 9.
Figure 11:
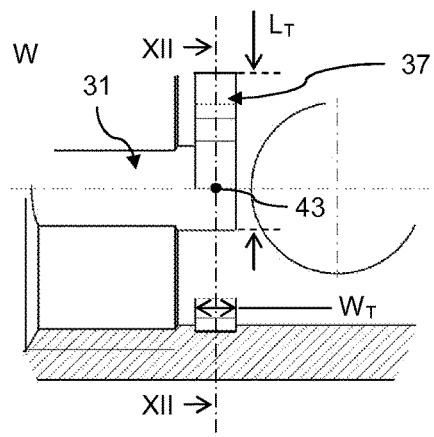
FIG. 11 is a detail W of the cross-sectional side view of FIG. 10.
Figure 12:
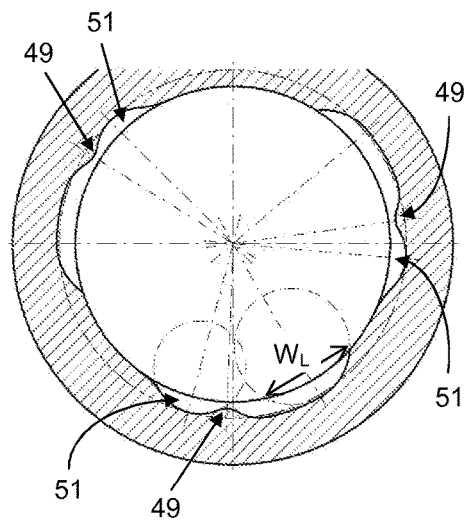
FIG. 12 is a cross-sectional view of the intramedullary nail of FIG. 11 taken along line XII-XII in FIG. 11.
Figure 13:
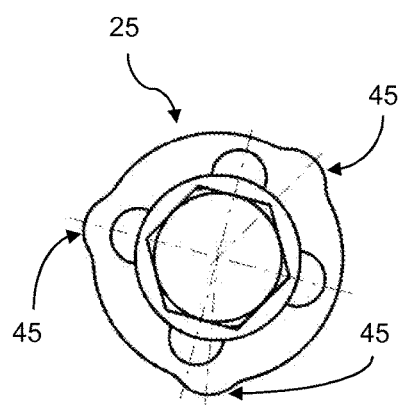
FIG. 13 is a top view of an insert sleeve insertable into the intramedullary nail of FIG. 9.

Specifically, the inner wall 19 of the cavity 17 is provided with a longitudinal groove 31 having a proximal end 33 and a distal end 35 (shown in FIGS. 10 and 11 in connection with the other embodiment only). The longitudinal groove 31 is axially open at its proximal end and accessible therethrough and extends along the cavity longitudinal axis 23 in distal direction. The inner wall 19 is further provided with a transverse groove 37 having a communicating end 39 and a terminal end 41 and extending perpendicularly to the cavity longitudinal axis 23. The longitudinal and transverse grooves 31, 37 form a right-angled wedge, wherein the longitudinal and transverse grooves 31, 37 join into each other at a junction 43 (shown in FIGS. 10 and 11 in connection with the other embodiment only) where the distal end 35 of the longitudinal groove 31 and the communicating end 39 of the transverse groove 37 join into each other.

Further, the insert sleeve 25 includes a cam 45 that is arranged at the proximal end of the insert sleeve 25 and that protrudes from the insert sleeve 25 in radial direction. The cam 45 is axially insertable into the longitudinal groove 31 through the proximal axial opening of the longitudinal groove 31. The cam 45 matingly engages the longitudinal and transverse grooves 31, 37 when the insert sleeve 25 is coaxially inserted into the cavity 17 and rotated from the junction 43 into the locked position defined by the terminal end 41 of the transverse groove 37 and being snugly received in a seat described below, respectively.

The longitudinal and transverse grooves 31, 37 have a length $L_L$ and $L_T$, a width $W_L$ and $W_T$, and a depth $D_L$ and $D_T$, respectively. The depth of $D_L$, $D_T$ of the longitudinal and transverse grooves 31, 37 is defined by a radial distance between the inner wall 19 and a respective groove base 47 of the longitudinal and transverse grooves 31, 37. In the present embodiment, the depths $D_L$ and $D_T$ are identical.

As can be taken from FIG. 5, the groove base 47 of the transverse groove 31 comprises a hump 49 which extends radially inwardly and thus reduces the depth of the transverse groove 37 locally. The hump 49 is configured and sized to reversibly and radially inwardly displace and deform the cam 45 when the insert sleeve 25 is rotated into the locked position. After having passed the hump 49, the cam 45 is received in a seat 51 of the transverse groove 37 which defines the locked position of the insert sleeve 25. The seat 51 is arranged between the hump 49 and the terminal end 39 of the transverse groove 37, i.e. the seat 51 is delimited from the communicating end 39 of the transverse groove 31 by the hump 47. Further, each of the longitudinal groove 31 and the seat 51 is curved as a circular arc in cross-sectional view of the nail.

The depth of the transverse groove 37 is smaller at the seat 51 than at the communicating end 39 and likewise smaller than the depth of the longitudinal groove 31 at the junction 43. In addition, the length of the seat 51 is smaller than the width of the longitudinal groove 31. This allows the cam 45 to be compressedly and thus form-fittedly and/or press-fittedly received in the seat 51 which in turn ensures that the insert sleeve 25 is fixedly received in the cavity 17 of the intramedullary nail 11.

As can be taken from FIGS. 6 and 7, in addition, the insert sleeve 25 is provided with a reception 53 for engagement of a tool for inserting the insert sleeve 25 into the cavity 17 and also with a reception 55 for rotating the insert sleeve from the inserted but unlocked intermediate position into the locked position.

Referring to FIGS. 9 to 13, another exemplary embodiment of an intramedullary nail assembly in accordance with the teachings of the present disclosure is shown. In this embodiment, the inner wall 19 of the cavity 17 is provided with three at least substantially identical sets of longitudinal and transverse grooves 31, 37 and the insert sleeve 25 comprises three at least substantially identical cams 45 radially protruding from it. The distribution of the sets of longitudinal and transverse grooves 31, 37 in circumferential direction around the cavity longitudinal axis 23 is identical to the distribution of the cams 45 in circumferential direction around the insert longitudinal axis 27. The distances between neighboring sets of longitudinal and transverse grooves 31, 37 and likewise between neighboring cams 45 vary such that the insert sleeve 25 may be received within the cavity 17 in a single rotational orientation only.

While this disclosure has been described as having exemplary designs, the present disclosure can be further modified within the spirit and scope of this disclosure. This application is therefore intended to cover any variations, uses, or adaptations of the disclosure using its general principles. Further, this application is intended to cover such departures from the present disclosure as come within known or customary practice in the art to which this disclosure pertains and which fall within the limits of the appended claims.

REFERENCE NUMERAL LIST 11 intramedullary humeral nail
13 nail longitudinal axis
15 transverse throughhole
17 cavity
19 nail inner wall
21 head space
23 cavity longitudinal axis
25 insert sleeve
27 insert longitudinal axis
29 locking hole
31 longitudinal groove
33 proximal end
35 distal end
37 transverse groove
39 communicating end
41 terminal end
43 junction
45 cam
47 groove base
49 hump
51 seat
53 reception
55 reception
$D_L$ depth
$D_T$ depth
$L_L$ length
$L_T$ length
$W_L$ width
$W_T$ width
W detail

The invention claimed is:
1. An intramedullary nail assembly, comprising:
an intramedullary nail, and
an insert sleeve,
the intramedullary nail having a nail longitudinal axis and comprising a cavity being accessible from a nail proxi- mal end, the cavity being confined by a nail inner wall, the cavity having a cavity longitudinal axis, wherein the nail inner wall is provided with a predominantly longitudinal groove and a predominantly transverse groove, the transverse groove having a terminal end and a communicating end, and the longitudinal groove having a proximal end and a distal end, the transverse groove and the longitudinal groove joined together at a junction where the distal end of the longitudinal groove intersects the communicating end of the transverse groove, each of the grooves having a length, a width, and a depth, the longitudinal groove being accessible from a cavity proximal end, and wherein the insert sleeve is configured to be received within the cavity and comprises a cam, the cam radially protruding from the insert sleeve and sized to mate with each of the longitudinal and transverse grooves such that the cam is displaceable within the longitudinal groove from the proximal end of the longitudinal groove to the junction, and is further displaceable from the junction towards the terminal end of the transverse groove such that the cam resides entirely within the transverse groove.

2. The intramedullary nail assembly of claim 1,
wherein the longitudinal groove extends in parallel to the cavity longitudinal axis or the transverse groove extends orthogonally to the cavity longitudinal axis.

3. The intramedullary nail assembly of claim 1,
wherein the longitudinal groove and the transverse groove form a right angle with each other.

4. The intramedullary nail assembly of claim 1,
wherein at least a section of the transverse groove forms a seat for receiving the cam in a locked position, and wherein the transverse groove comprises a groove base, the groove base, along a part of the length of the transverse groove, extending radially inwardly thus reducing the depth of the transverse groove such as to form a hump within the transverse groove.

5. The intramedullary nail assembly of claim 4,
wherein the hump is arranged between the junction and the terminal end of the transverse groove, the hump being configured and sized to reversibly and radially inwardly displace or deform the cam of the insert sleeve while the cam travels from the junction towards the terminal end of the transverse groove.

6. The intramedullary nail assembly of claim 5,
wherein the hump is arranged between the seat and the junction, and units the seat from the junction.

7. The intramedullary nail assembly of claim 6,
wherein the seat is formed between the hump and the terminal end of the transverse groove.

8. The intramedullary nail assembly of claim 7,
wherein the seat has a length and a depth and the longitudinal groove has a width and a depth at the junction, and wherein at least one of the following conditions is fulfilled:
a) the width of the longitudinal groove at the junction with the transverse groove is greater than the length of the seat;
b) the depth of the longitudinal groove at the junction with the transverse groove is greater than the depth of the seat.

9. The intramedullary nail assembly of claim 1,
wherein the nail inner wall is provided with a plurality of sets of predominantly longitudinal and predominantly transverse grooves, the insert sleeve having a same plurality of cams radially protruding from it, a circumferential distribution of the cams being the same as that of the sets of grooves, each cam being sized to matingly engage a respective set of grooves.

10. The intramedullary nail assembly of claim 9,
wherein the plurality of sets of grooves and the plurality of cams are unevenly distributed in a circumferential direction such that each cam is unambiguously assigned to a set of grooves and the insert sleeve may only be received within the cavity in a well-defined circumferential orientation.

11. The intramedullary nail assembly of claim 1,
wherein the insert sleeve and the cavity have cross sectional dimensions adapted to each other such that the insert sleeve is received within the cavity essentially without play.

12. The intramedullary nail assembly of claim 1,
wherein the intramedullary nail and the insert sleeve comprise at least one transverse throughhole and at least one transverse locking hole, respectively, wherein the positions and axes of a respective transverse locking hole and a respective transverse throughhole coincide in a locked position of the insert sleeve.

13. The intramedullary nail assembly of claim 1, wherein the longitudinal groove extends in parallel to the cavity longitudinal axis and the transverse groove extends orthogonally to the cavity longitudinal axis.

14. The intramedullary nail assembly of claim 1, wherein at least a section of the transverse groove forms a seat for receiving the cam in a locked position, or the transverse groove comprises a groove base, the groove base, along a part of the length of the transverse groove, extending radially inwardly thus reducing the depth of the transverse groove such as to form a hump within the transverse groove.

15. An intramedullary nail assembly, comprising:
an intramedullary nail; and
an insert sleeve;
the intramedullary nail having a nail longitudinal axis and comprising a cavity being accessible from a nail proximal end, the cavity being confined by a nail inner wall, the cavity having a cavity longitudinal axis, wherein the nail inner wall is provided with a predominantly longitudinal groove and a predominantly transverse groove, the transverse groove and the longitudinal groove communicating with each other at a junction common to the longitudinal groove and the transverse groove, each of the grooves having a length, a width, and a depth, the longitudinal groove being accessible from a cavity proximal end, and wherein the insert sleeve is configured to be received within the cavity and comprises a cam, the cam radially protruding from the insert sleeve and sized to mate with each of the longitudinal and transverse grooves such that the cam is displaceable within the longitudinal groove from a longitudinal groove proximal end to the junction and is further displaceable towards a terminal end of the transverse groove;
wherein at least a section of the transverse groove forms a seat for receiving the cam in a locked position, and wherein the transverse groove comprises a groove base, the groove base, along a part of the length of the transverse groove, extending radially inwardly thus reducing the depth of the transverse groove such as to form a hump within the transverse groove.

16. An intramedullary nail assembly, comprising:
an intramedullary nail; and
an insert sleeve;

the intramedullary nail having a nail longitudinal axis and comprising a cavity being accessible from a nail proximal end, the cavity being confined by a nail inner wall, the cavity having a cavity longitudinal axis, wherein the nail inner wall is provided with a predominantly longitudinal groove and a predominantly transverse groove, the transverse groove and the longitudinal groove communicating with each other at a junction common to the longitudinal groove and the transverse groove, each of the grooves having a length, a width, and a depth, the longitudinal groove being accessible from a cavity proximal end, and wherein the insert sleeve is configured to be received within the cavity and comprises a cam, the cam radially protruding from the insert sleeve and sized to mate with each of the longitudinal and transverse grooves such that the cam is displaceable within the longitudinal groove from a longitudinal groove proximal end to the junction and is further displaceable towards a terminal end of the transverse groove;

wherein the nail inner wall is provided with a plurality of sets of predominantly longitudinal and predominantly transverse grooves, the insert sleeve having a same plurality of cams radially protruding from it, a circumferential distribution of the cams being the same as that of the sets of grooves, each cam being sized to matingly engage a respective set of grooves.

\* \* \* \* \*

UNITED STATES PATENT AND TRADEMARK OFFICE
CERTIFICATE OF CORRECTION

PATENT NO. : 9,775,655 B2  
APPLICATION NO. : 14/633436  
DATED : October 3, 2017  
INVENTOR(S) : Schwammberger et al.

Page 1 of 1

It is certified that error appears in the above-identified patent and that said Letters Patent is hereby corrected as shown below:

On the Title Page

In item (30), in "Foreign Application Priority Data", in Column 1, Line 1, delete "14162715" and insert --14162715.8-- therefor In the Claims In Column 9, Line 49, in Claim 6, delete "units" and insert --delimits-- therefor Signed and Sealed this  
Twenty-eighth Day of May, 2019

Andrei Iancu  
*Director of the United States Patent and Trademark Office*